United States Patent [19]

Schroeder

[11] Patent Number: 5,152,774
[45] Date of Patent: Oct. 6, 1992

[54] SURGICAL INSTRUMENT HAVING A TOUGHENED WEARING SURFACE AND METHOD OF MAKING THE SAME

[76] Inventor: William A. Schroeder, 16141 Weatherly Way, Huntersville, N.C. 28078

[21] Appl. No.: 522,247

[22] Filed: May 11, 1990

Related U.S. Application Data

[63] Continuation-in-part of Ser. No. 286,166, Dec. 19, 1988, abandoned, which is a continuation-in-part of Ser. No. 258,841, Oct. 17, 1988, abandoned.

[51] Int. Cl.$^5$ .................. A61B 17/28; A61B 17/32
[52] U.S. Cl. ...................................... 428/457; 606/1; 606/205; 606/174; 427/2; 427/250; 427/248.1; 148/537
[58] Field of Search ................ 606/1, 174, 167, 205, 606/208, 207; 427/42, 25 P, 2

[56] References Cited

FOREIGN PATENT DOCUMENTS 59-76872 5/1984 Japan .
621476 2/1981 Switzerland .

OTHER PUBLICATIONS

Balzers Tool Coating, Inc. Sales Brochure Published Approximately Jan. 1987.
Niagara Cutter Titanium Nitride Coated Milling Cutters Mar. 1, 1984.

*Primary Examiner*—Michael H. Thaler
*Attorney, Agent, or Firm*—Ralph H. Dougherty

[57] ABSTRACT

A method for making a stainless steel or titanium surgical instrument having a high toughness wearing surface, by vapor deposition of titanium nitride thereon in a vacuum chamber having a molten evaporant in a hearth in the bottom of the chamber, and using the hollow cathode effect. A preferred method includes tempering the instrument at temperatures above 200° C., then coating by physical vapor deposition at temperatures from about 175° to 260° C. Ring handled instruments with box lock pivots are coated before assembly. Toughened surgical instruments are also disclosed.

13 Claims, 1 Drawing Sheet

SURGICAL INSTRUMENT HAVING A TOUGHENED WEARING SURFACE AND METHOD OF MAKING THE SAME

CROSS REFERENCE TO RELATED APPLICATIONS

This application is a continuation-in-part of my co-pending U.S. patent application Ser. No. 286,166, filed Dec. 19, 1988, abandoned, which is a continuation-in-part of U.S. patent application Ser. No. 258,841, filed Oct. 17, 1988, abandoned.

BACKGROUND OF THE INVENTION

This invention relates to the field of surgical instruments, particularly instruments which come into contact with other instruments or other portions of an instrument during use or storage, such as instruments having teeth, serrations, a cutting edge, or being otherwise susceptible to wear. Most particularly, the invention relates to a method for making high toughness surgical scissors and a method for imparting such toughness to them.

Surgical cutting instruments, in particular scissors, must give a sharp clean cut in order to prevent unexpected and unwanted damage to delicate tissues. When surgical instruments are being handled in groups, particularly during a sterilization process, they frequently come in contact with one another which can tend to dull a cutting edge. In addition, when scissors are in use, each cut generally tends to dull the cutting edge as it contacts the adjacent blade. Thus it is highly desirable to provide a toughened wearing surface on a surgical instrument to prevent the frequent necessity for sharpening the instrument. In addition, each sharpening removes a small amount of metal until the instrument must eventually be discarded.

Presently available surgical scissors have an average useful life of about three years, because of the limited life of the cutting edge. Heretofore, attempts to increase this limited useful life have included using high quality stainless steels and tungsten carbide inserts on cutting surfaces, particularly on surgical scissors. The present invention provides a surgical instrument have a tough wearing surface with a useful life of at least double that of presently available instruments. In addition, sharpening of such instruments is sharply curtailed with attendant cost savings, and reduced repairs.

Titanium nitride is both inert and has a high degree of lubricity, which makes titanium nitride coated stainless steel the ideal material for surgical instruments, as they give the surgeon excellent control of the instrument during surgery by reducing resistance during cutting, and promoting release of tissue, as well as avoiding contamination or infection from foreign substances.

Instruments with members that are connected by box locks generally accumulate blood in the region of the box locks during use. Such blood becomes caked and tightly adherent. The instruments are usually cleaned by ultrasound, but this does not always break loose the dried and nearly crystallized blood. In addition, over a period of time cleaning by ultrasound promotes the formation of cracks within these box locks. Instruments utilizing box locks are generally discarded either because of blood caking in multiple layers or crack formation which also retains blood. By coating all parts of a box lock with titanium nitride before assembly, the lubricity of the titanium nitride resists adherance of dried blood, as well as cooperating with the ultrasound cleaning treatment to promote removal of dried blood from the instrument.

SUMMARY OF THE INVENTION

The present invention is a method for making a toughened surgical scissor or other surgical instrument having a metallurgical composition of either stainless steel or titanium, treated by vapor deposition of metal nitride thereon in a vacuum chamber having a molten evaporant in a hearth in the bottom of the chamber, and using the hollow cathode effect. The vapor deposition temperature can be in a range of from about 175° to 260° C., but advantageously is about 215 degrees. Scissors and tempered or hardened instruments which are tempered at temperatures above 200C. should be coated at vapor deposition temperatures from about 175 to about 225C., and preferably about 200C. The interior of the chamber contains a nitrogen atmosphere. The vacuum within the chamber is from about $1 \times 10^{-3}$ Tor to about $10 \times 10^{-3}$ Tor, but preferably about $5 \times 10^{-3}$ Tor. By the hollow cathode effect, the evaporant is attracted to the substrate article and adheres thereto. The evaporant is preferably titanium, a titanium nitride alloy, or zirconium.

The coating temperature is critical to the operability of stainless steel and titanium surgical instruments which have been TiN coated by vapor deposition. Prior to the present invention, there had been no low temperature (in the range of 175 to 260C.) TiN coating of stainless steel surgical instruments by physical vapor deposition, since it was thought throughout the industry that low temperature vapor deposition was not suitable for good coating adherence or durability.

OBJECTS OF THE INVENTION

It is the principal object of this invention to provide a surgical instrument having a high toughness wearing surface.

It is also an object of this invention to provide a surgical instrument having a cutting edge which does not need frequent sharpening.

It is another object of this invention to provide surgical scissors with a longer useful life between sharpenings than are currently available.

It is another object of this invention to provide high toughness surgical instruments for microsurgical use.

It is also an object of this invention to provide coated surgical instruments which give a surgeon excellent control of the instrument during surgery by reducing resistance during cutting.

It is also an object of this invention to provide a method for making nitride coated surgical instruments without softening the base material during tempering.

It is also an object of this invention to provide a surgical instrument having improved cleanability.

It is also an object of this invention to provide a surgical instrument having both tungsten carbide inserts on cutting surfaces and high lubricity.

It is also an object of this invention to provide a titanium surgical instrument which will retain a gold color.

BRIEF DESCRIPTION OF THE DRAWINGS

The foregoing and other objects will become more readily apparent by reference to the following detailed description and the appended drawings in which.

DETAILED DESCRIPTION

Figure 1:
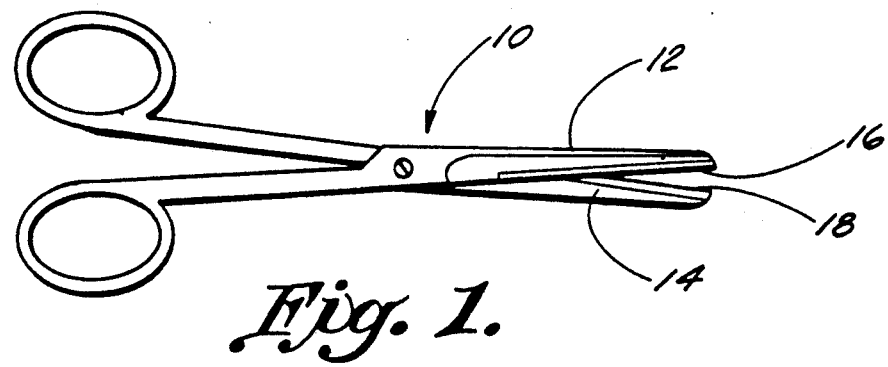
FIG. 1 is a plan view of a pair of rounded blade end surgical scissors in accordance with the invention.

Referring now to FIG. 1, surgical scissors 10 have a pair of oppositely disposed blades 12 and 14 with respective cutting edges 16 and 18. The blade material is stainless steel, having a composition in the range of 5 to 30 percent (%) chromium (preferably 7 to 25% chromium), about 3 to 23% nickel (preferably 5 to 19%), 0 to 10% molybdenum, balance iron and incidental impurities. Such stainless steels include, without limitation, ferritic, martensitic, and austenitic stainless steels. Alternatively, the instrument can be titanium.

The blades receive a nitriding treatment by vapor deposition, preferably coating by physical vapor deposition at temperatures from about 175 to about 260C., preferably about 200C., of titanium nitride (TiN). Titanium is placed in the hearth of a vacuum chamber in molten form. The scissor blades are placed in the chamber (prior to scissor assembly) above the hearth as the substrate. The molten titanium is vaporized in a nitrogen atmosphere and physically deposited onto the desired surface, the wearing surface, of the substrate in the form of titanium nitride by the hollow cathode effect. The entire article is advantageously coated, but it is possible to coat only a specific portion thereof by proper masking, if desired. The titanium nitride coating is preferably about 2 microns in thickness, and has a gold color.

Scissors, and tempered or hardened instruments which are tempered by heat treating at temperatures above 200C., should be coated at vapor deposition temperatures from about 175 to about 225C., and preferably about 200C. Coating at low temperatures will avoid the softening effect which occurs to stainless steel when coated at temperatures in excess of 260 degrees Celsius.

The theory to which the applicant subscribes, but does not wish to be held, is that the titanium nitride both coats and diffuses into the stainless steel, creating a very high toughness surface. It is believed that the vaporized particles react with the steel, altering its molecular structure up to a depth of about 2 to 5 microns. The nitrided portion of the instrument has an increased Rockwell "C" hardness above that of the substrate. When the substrate is titanium, it is subject to discoloration from any heat treatment, including sterilizing in an autoclave, and generally has a beginning hardness of about 39 to about 44. The low temperature coating process both increases the substrate hardness, up to about 50, and provides a permanent gold color.

Vapor deposition at low temperatures is more costly than at higher temperatures, because of the unavailability (and attendant higher cost) of low temperature coating machines. The reason for coating at low temperatures is to avoid softening the substrate. When coated at temperatures at or above 480C., stainless steel instruments with a Rockwell "C" hardness of about 52 are softened, often to below a Rockwell "C" hardness of 30.

The following Table shows the resulting substrate hardness on the Rockwell "C" scale of stainless steel coated at the temperatures indicated.

TABLE

| Starting Hardness | Vapor Deposition Temperature | Final Hardness |
| --- | --- | --- |
| 50 | 175 C. | 50 |
| 50 | 204 C. | 51 |
| 50 | 210 C. | 52 |
| 50 | 216 C. | 54 |
| 50 | 225 C. | 52 |
| 50 | 260 C. | 47 |
| 50 | 316 C. | 43 |
| 50 | 482 C. | 28 |

The vapor deposition temperature should be from 175 to 260C. (347 to 500F.) in order to avoid substantial softening of the instrument. As surprisingly shown by the Table, vapor deposition temperatures from 175 to 225 actually increase the hardness of the instrument. The mechanism which accomplishes this hardness increase is believed to be similar to the metallurgical strengthening effect known as "double drawing".

Scissors or other instruments with metal-to-metal surfaces should be micro-smooth, that is, the substrate for such instruments should be smoothed by grinding or polishing prior to coating, preferably to a mirror finish, so the coating will also be smooth and without high spots, even microscopic high spots, which will extend the wear life of the coating.

ALTERNATIVE EMBODIMENTS

Figure 2:
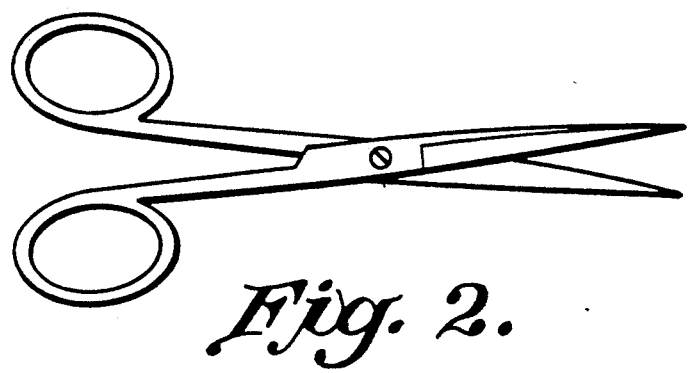
FIG. 2 is a plan view of a alternative style of surgical scissors, having one blade end pointed and one blade end blunt, toughened in accordance with the invention.
Figure 3:
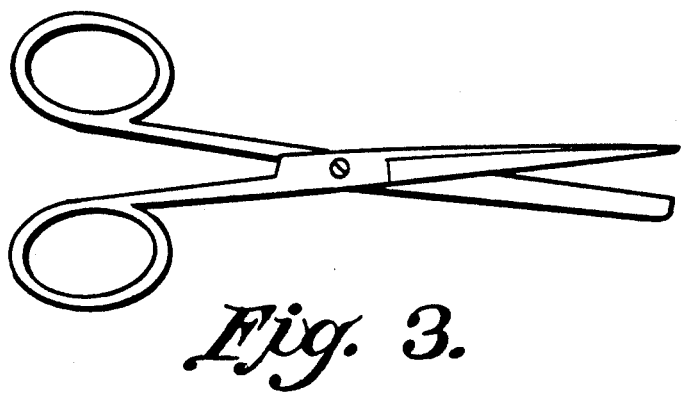
FIG. 3 is a plan view of a second alternative style of surgical scissors in accordance with the invention.
Figure 4:
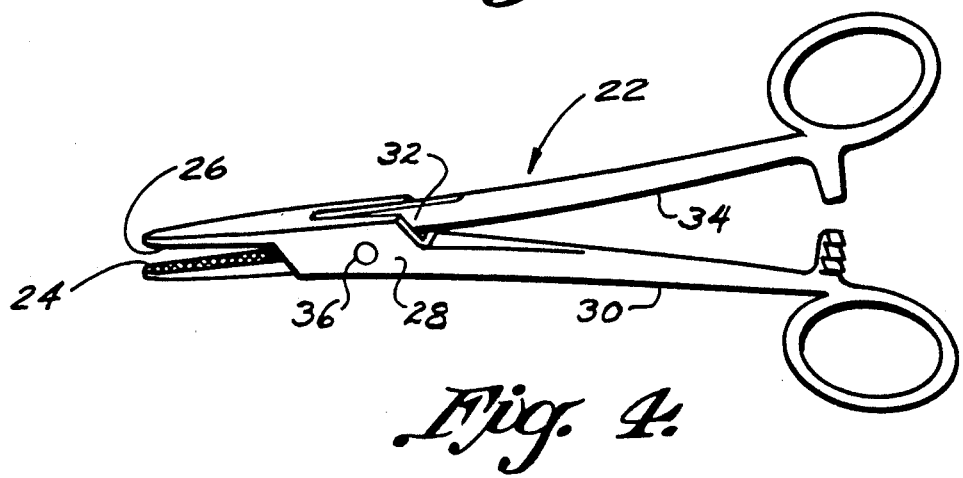
FIG. 4 is a plan view of a pair of needle holders in accordance with the invention, and having a box lock type pivotal connector arrangement.

FIG. 2 shows a scissors with both blades pointed, FIG. 3 shows a scissors with one blade pointed and one blade blunt, whereas FIG. 4 shows a needle holder, all of which are coated in accordance with the invention to provide a high toughness, high lubricity coating on at least the wearing surfaces. The needle holder 22 has opposed cross-hatched faces 24 and 26, which are similar to the manner of file or rasp faces. The needle holder (as do many ring-handle instruments) has a box lock pivot and attachment means wherein female portion 28 of one member 30 receives the male connector portion 32 of the other member 34. Pin 36 acts as both connector and pivot for the box lock. All parts of the box lock are coated with titanium nitride before assembly. The coating thickness of pin 36 preferably is from about 0.0001 to about 0.001 inch, but most preferably about 0.0001 inch. The circumference of the pivot pin 36 is the principal wearing surface of the instrument. The coating both promotes ease of assembly of the instrument, and ease of operation. The pivot pin normally is attached in the same manner as a drift pin, by being pressed or forced into a receiving hole in the male member under pressure, and it extends into both sides of the female member, which acts as the journal or bearing for the pin.

The embodiment of FIG. 3 shows one scissor blade 19 with a tungsten carbide insert 20. The other blade can also be provided with a mating tungsten carbide insert on the cutting edge. The present invention also comprehends the coating of a surgical instrument containing such insert on either one or both cutting edges with titanium nitride in accordance with the disclosed method. This will result in the benefits of added toughness and long life to the instrument, as well as reducing or limiting wear and increasing lubricity of the wearing surfaces.

"Surgical scissors", as used herein, means straight, curved, acutely curved and very acutely curved scissors for surgical use. The invention is equally applicable to other stainless steel or titanium surgical instruments, including, without limitation, cutting instruments, grasping and holding instruments, electrosurgical instruments, cautery instruments, needle holders, osteotomes and periosteotomes, chisels, gouges, rasps, files, saws, reamers, wire twisting forceps, wire cutting forceps, ring handled forceps, tissue forceps, cardiovascular clamps, and rongeurs.

Any stainless steel or titanium instrument having teeth, serrations, a cutting edge, or being otherwise susceptible to wear, is capable of developing a high toughness wearing surface in accordance with this invention.

Suitable alternative coating materials are titanium nitride (TiN) and zirconium nitride (ZrN).

SUMMARY OF THE ACHIEVEMENTS OF THE OBJECTS OF THE INVENTION

From the foregoing, it is readily apparent that I have provided a surgical instrument having a wearing surface with high toughness, a surgical instrument having a cutting edge with high lubricity which does not need frequent sharpening, which gives excellent control to a surgeon using the instrument, a surgical scissors with a longer useful life between sharpenings than are currently available, and a method for making such toughened instrument, and for imparting to it an attractive gold color, which will not discolor during further heat treatments.

It is to be understood that the foregoing description and specific embodiments are merely illustrative of the best mode of the invention and the principles thereof, and that various modifications and additions may be made to the invention by those skilled in the art, without departing from the spirit and scope thereof, thus the invention is to be limited only by the scope of the appended claims.

What is claimed is:

1. A method for making surgical instruments, comprising the steps of:
    providing a stainless steel or titanium surgical instrument having a wearing surface; and
    providing a nitride coating on the wearing surface by vapor deposition of a nitride selected from the group consisting of titanium nitride, titanium nitride alloy and zirconium nitride, at a vapor deposition temperature of from 175 to 225C. (347 to 437F.);
    whereby the nitrided portion of the instrument has a resulting Rockwell "C" hardness of at least about 50.

2. A method according to claim 1, further comprising tempering said instrument at a temperature above 200C. prior to coating.

3. A method according to claim 1 wherein the vapor deposition is conducted at a vacuum of at least $5 \times 10^{-3}$ atmospheres.

4. A metal according to claim 1 wherein said surgical instrument is a surgical cutting instrument.

5. A method according to claim 4 wherein said surgical instrument is a surgical scissor, and said wearing surface is a scissor blade.

6. A method according to claim 1 further comprising smoothing said wearing surfaces to a micro-smooth finish.

7. A method according to claim 6 wherein said smoothing is accomplished by grinding or polishing the prior to coating of the instrument, thereby extending the wear life of the coating.

8. A method according to claim 1 wherein said surgical instrument is a grasping or holding device.

9. A method according to claim 1 wherein said surgical instrument has cooperating members connected by a box lock, including a pivot pin, said method further comprising providing a titanium nitride coating on all portions of the box lock including the pivot pin before assembly of the instrument.

10. A method according to claim 9, wherein the pivot pin is provided with a coating having a thickness of from about one thousandth to about one ten-thousandth of an inch.

11. A method according to claim 10, wherein the pivot pin is provided with a coating having a thickness of about one ten-thousandth of an inch.

12. A method of making a tempered surgical instrument having a toughened wearing surface, comprising:
    forming an instrument from a metal selected from the group consisting of stainless steel and titanium;
    tempering said instrument at a temperature about 200 C. for a sufficient period of time to harden the metal to a desired hardness; and
    coating the wearing surface of said instrument by physical vapor deposition of an evaporant at a temperature of from about 175 to 225 C.;
    the evaporant being selected from the group consisting of titanium, titanium nitride alloy, and zirconium.

13. A surgical instrument article having a toughened wearing surface, said wearing surface being toughened according to the method of claim 12.

* * * * *